United States Patent [19]
Kim

[11] 3,993,077
[45] Nov. 23, 1976

[54] METHOD AND APPARATUS RELATING TO THE PRACTICE OF ACUPUNCTURE

[76] Inventor: Sung S. Kim, 6110 Manchester, Fort Wayne, Ind. 46815

[22] Filed: Dec. 26, 1974

[21] Appl. No.: 536,543

[52] U.S. Cl. .......... 128/329 A
[51] Int. Cl.² .......... A61B 17/34
[58] Field of Search .......... 24/255 TZ, 260; 128/329, 330

[56] References Cited

UNITED STATES PATENTS

| | | | |
|---|---|---|---|
| 102,262 | 4/1870 | Herrick | 128/329 A UX |
| 134,756 | 1/1873 | Marston | 24/260 X |
| 590,401 | 9/1897 | Morgan | 24/260 |
| 1,515,860 | 11/1924 | Howard | 24/260 UX |
| 3,856,019 | 12/1974 | Waller | 128/329 A |

*Primary Examiner*—Channing L. Pace
*Attorney, Agent, or Firm*—Albert L. Jeffers

[57] ABSTRACT

A special acupuncture needle and a method and apparatus for inserting the needle. The needle is adapted for placement in a selected region, especially in the external ear, and consists of a pair of opposed curved pointed sections which can be pressed together to effect insertion of the needle. An inserting device is provided for pressing the needle into the proper position while pressing the aforementioned opposed curved portions together, thereby to fix the needle in place. The needle has a portion which is exposed when the needle is implanted and which exposed portion has a handle, or the like, connected thereto for movement of the needle to stimulate the region in which the needle is implanted, thereby permitting the individual in whose external ear the needle is implanted effectively to carry out self-treatment merely by manipulating the handle on the exposed portion of the needle.

5 Claims, 14 Drawing Figures

METHOD AND APPARATUS RELATING TO THE PRACTICE OF ACUPUNCTURE

The present invention relates to acupuncture treatment and is particularly concerned with a special form of needle adapted for remaining in inserted position and to a method of and a device for effecting the insertion. The present invention further relates to a needle construction which permits the individual having the inserted needle to stimulate the region in which the needle is inserted by manual manipulation thereof.

Acupuncture treatments are known and it has been developed that there are numerous regions of the external ear which can be stimulated by the insertion of acupuncture needles therein, and certain desired results obtained thereby. Obesity, for example, has been treated in this manner.

It is often the case, however, that the proper placement of the acupuncture needle is difficult and requires highly skilled personnel for locating the proper region and for effecting the insertion of the needle. Further, in cases where continuing treatment is necessary, the patient is often required to make repetitive visits for reinsertion of a needle, and the like.

In particular, in respect of the ear, the placement of a needle in the proper place in the proper manner has been quite difficult. In one known method, a staple-like needle element is inserted in a desired region of the external ear and the ends of the staple are crimped inwardly to form a more or less permanent placement of the acupuncture needle element in the external ear. The placement of a staple in the aforesaid manner is attended with considerable difficulties in respect of manipulating the inserting device, and in effecting crimping of the staple while, furthermore, some considerable tissue damage accompanies needle insertion of this nature so that the possibility of considerable discomfort and the possibility of infection present themselves.

With the foregoing in mind, a primary objective of the present invention is the provision of a special acupuncture needle element, or clip, which can be inserted with the minimum of tissue damage and discomfort to the patient.

Another object is the provision of a special acupuncture needle element, or clip, which can readily be removed from implanted position without discomfort to the patient, and without tissue damage.

Still another object is the provision of an acupuncture needle element adapted, after implacement, for manipulation by the patient for effecting stimulation of the region in which the needle is implanted.

A still further object is the provision of a specialized acupuncture needle element, especially for being implanted in a selected region of the external ear, which is easy to implant and which causes the least discomfort to the patient and the insertion of which creates the least likelihood of infection.

Still another object is the provision of an implanting apparatus for implanting the special acupuncture needle of the present invention.

BRIEF SUMMARY OF THE INVENTION

According to the present invention, a special acupuncture needle is provided which consists of a pair of sharp prongs curved toward each other and having pointed ends in opposed relation. The prongs of the needle at the ends opposite the pointed ends are connected to a carrier element, or handle, to form a unitary structure. If desired, the handle or carrier element can be omitted and the needle itself can be used as a handle. The carrier element may have a keeper member in the form of a bead, or ring, slidable thereon which is adapted to press downwardly over the prongs of the needle to press the prongs together to effect insertion of the needle. At the same time, the keeper member engages recessed regions on the two prong members, or a latch device on the handle or carrier element, and holds the prongs together. The needle is in this manner implanted in the correct position with the keeper member holding the needle prongs together. With the needle thus more or less permanently implanted, stimulation of the region in which the needle is implanted can readily be accomplished by manual manipulation of the aforementioned carrier element or handle. The keeper member is, advantageously, readily frangible, or severable, so that the needle according to the present invention can readily be removed when desired, or when necessary, merely by breaking, or cutting, the keeper therefrom and withdrawing the prongs of the needle from implanted position with simultaneous separation thereof.

The implanting device comprises a holder which is adapted for receiving the needles in one end with the prongs separated and having foot portions adjacent the needle so the inserting device can be located with the feet distributed around the region in which the needle is to be implanted. The device includes a plunger therein which can be actuated when the device is in the proper position to push the needle against the region in which it is to be implanted while simultaneously pushing the keeper member downwardly on the prongs of the needle, thereby to draw the prongs together. When the keeper member reaches a position along the prongs where it latches to the prongs, the insertion device can be withdrawn leaving the needle in implanted, or inserted, position.

The bead referred to above as a keeper member can be replaced by other types of devices for clamping the prongs in inserted position, such as a wire loop disposed in the plane of the prongs of the needle and having diametrally opposed holes therein, one of which is adapted for receiving the carrier element, or handle, which supports the prongs of the needle and the other of which is slidable along the prongs to push the prongs together and to latch on the prongs, or on the handle, when the needle is inserted. In the case of a wire member as a keeper, removal of the needle is accomplished by cutting the wire keeper to release the prongs from implanted position so the needle element can be withdrawn with simultaneous separation of the prongs thereof.

The objects of the present invention, as well as still other objects and advantages thereof, will become more apparent upon reference to the following detailed specification taken together with the accompanying drawings in which.

DETAILED DESCRIPTION OF THE INVENTION

Figure 1:
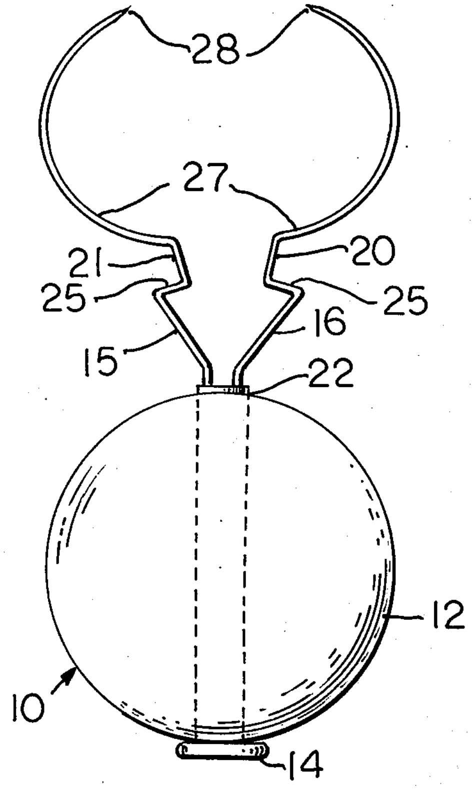
FIG. 1 is a view drawn at enlarged scale showing a needle according to the present invention before insertion.

Referring to the drawings somewhat more in detail, the needle element of the present invention, and generally indicated at 10, comprises a pair of curved prongs 27 having opposed pointed ends 28, with the needle prongs at the end opposite pointed ends 28 being embedded in a rod-like handle or carrier element 18, which may have a flat button-like outer end 14. The individual prongs diverge outwardly from the end of carrier member 18, as indicated at 15 and 16, and are then formed inwardly directly toward each other, as indicated at 25, and then have straight leg portions 20 and 21, which connect to the ends of the respective curved prongs 27 opposite the pointed ends 28 thereof.

A keeper member in the form of a hollow spherical bead member 12 is slidably mounted on carrier element 18 and has an aperture in one side in which handle 18 is slidable and another aperture 22 formed therein on the side facing the prongs of the needle element. When bead member 12 is moved from its FIG. 1 position to its FIG. 2 position, aperture 22 of the bead member slides along the diverging inclined portions 15 and 16 of the prongs and presses the prongs toward each other into implanted, or inserted, position. The bead will then snap over the portions 25 of the prongs and hold the prongs together, thus fixing the needle in implanted position. The bead member 12 and the carrier member, or handle, 18 with its flange like head 14 can be employed for manipulating the needle after it is implanted for stimulating the region in which the needle is implanted, thus permitting the individual in whom the needle is implanted effectively to carry out an acupuncture treatment.

It will be understood that, in as much as the needle penetrates tissue it is important for the needle to be sterile and for the region in which the needle is implanted to be maintained in a sanitary condition, such as by swabbing the region with alcohol, or the like, periodically.

Figure 2:
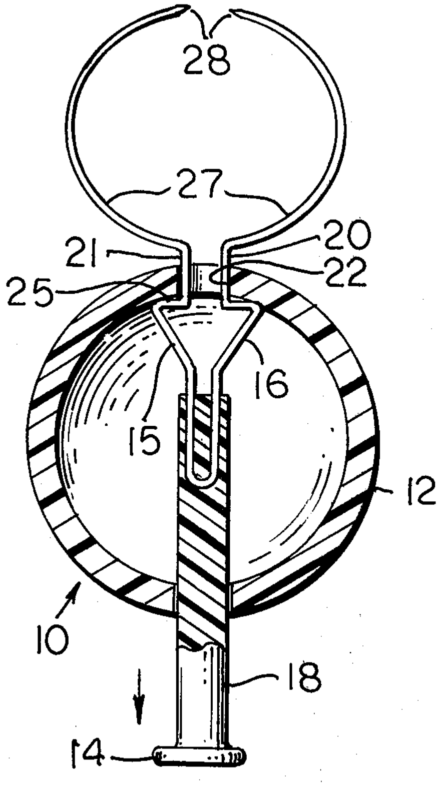
FIG. 2 is a view like FIG. 1 except drawn in section and showing the prongs of the needle clamped in the position occupied thereby when the needle is inserted.
Figure 3:
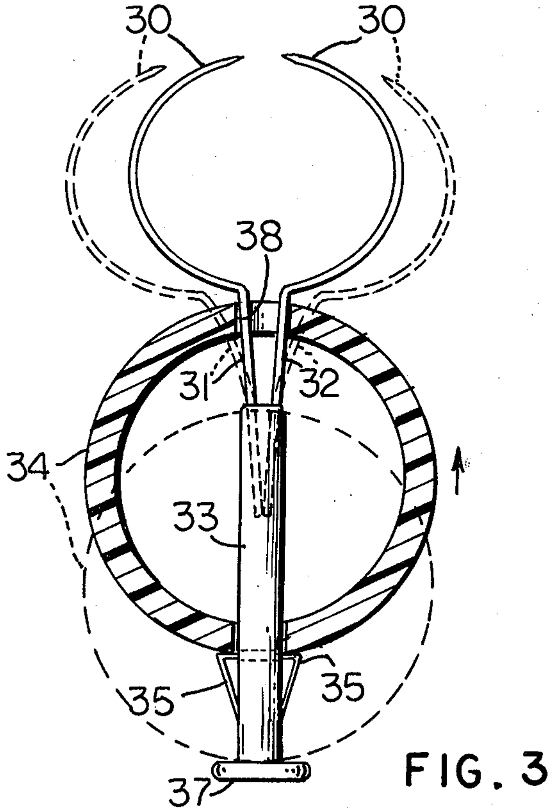
FIG. 3 is a view like FIG. 2 but showing a modified arrangement in which the keeper member clamps on the carrier element, or handle, of the needle instead of the needle prongs.

FIG. 3 shows a modification in which the needle element prongs 31 and 32 are connected to a carrier member, or handle, 33 and have curved outer ends 30 terminating in sharp points the same as the FIGS. 1 and 2 modifications except the prongs are rather simply shaped and are cammed into imbedded position by the aperture 38 formed in bead member 34 when it is advanced along handle 33 toward the pointed ends of the needle prongs.

The carrier member, or handle, 33 in FIG. 3 is provided with spring elements 35 which will snap outwardly behind the bead member when the bead member is advanced on the carrier member from the dashed position, in which it is shown in FIG. 3, up to the full line position in FIG. 3. The spring elements 35 thus form the retaining means for locking the bead member in advanced position on the carrier element 33.

FIGS. 4 through 7 show the device for implanting or inserting the needle of FIGS. 1 and 2, or the needle of FIG. 3. The implanting device is generally indicated at 110 and comprises a plunger 111 axially movable in a tubular body part 114, and having a pushbutton 112 on top, and which can be pressed downwardly by placing the fingers beneath flanges 118 on body part 114 and pressing downwardly on button 112 with the thumb. The plunger 111 is guided by spacers or ribs 123 and 124 which can be molded on the plunger, or molded on the inside of the tubular body part 114.

At the end of tubular part 114 opposite the protruding pushbutton 112 is a pair of axially extending spaced legs 128 adapted for connection to a rather short tubular waist member 115. Waist member 115 has three circumferentially spaced axial leg portions 116 which rest on the surface in which the needle is to be implanted in surrounding relation to the region. Screws 117 can be employed for connecting portions 128 to tubular waist member 115, thereby to permit tilting of the tubular body 114 on waist member 115, if necessary, to gain access to the region in which the needle is to be implanted. Mounted in tubular waist member 115 is a spring 120 having yieldable prongs 122.

Figure 6:
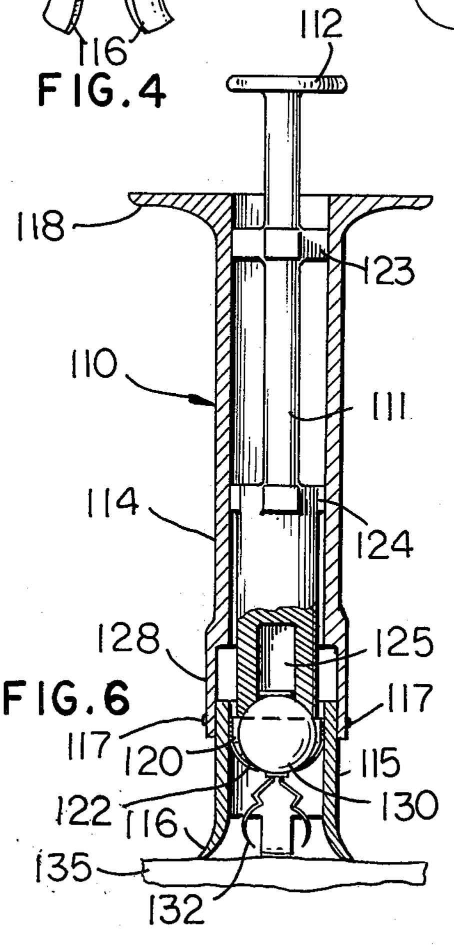
FIG. 6 is a sectional view through the insertion device, showing a needle therein preparatory to insertion of the needle.
Figure 7:
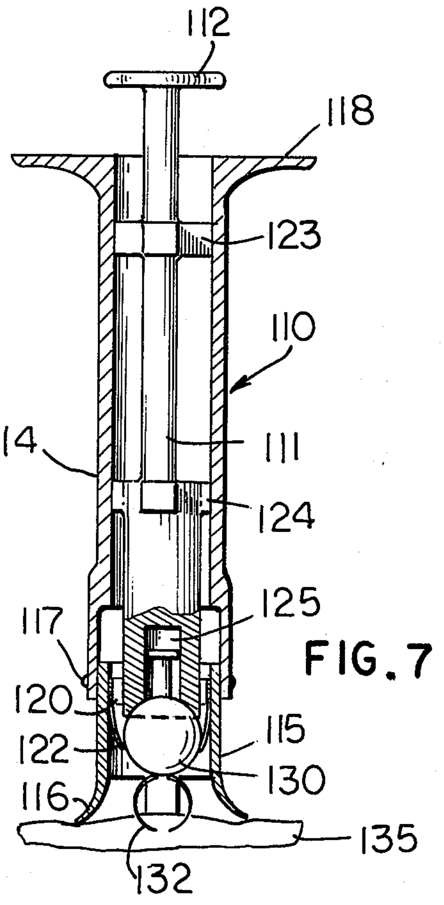
FIG. 7 is a view like FIG. 6, but shows the needle inserted and prior to removing the insertion device.

In operation, plunger 111 can be removed from the inserting device and a needle placed therein from the end opposite waist member 115. The plunger is then replaced so as to engage the bead portion of the needle as shown in FIG. 6. It will be noted that the end of plunger 111 adjacent the needle is formed with a cavity 125 into which the handle of the needle can be displaced, while the lower end of the plunger engages the bead of the needle. When the insertion device is properly located, the plunger 111 is moved from its FIG. 6 position to its FIG. 7 position and this will effect implanting, or insertion, of the needle, while at the same time the bead thereon is moved downwardly on the handle into the latched position on the needle structure that has been described above.

The insertion device can now be removed and the needle will remain implanted. During the insertion operation, the spring fingers 122 of spring 120 yield, as will be seen in FIG. 7, thereby permitting the aforementioned advancing movement of the bead and the withdrawing of the inserting device after insertion of the needle.

Figure 8:
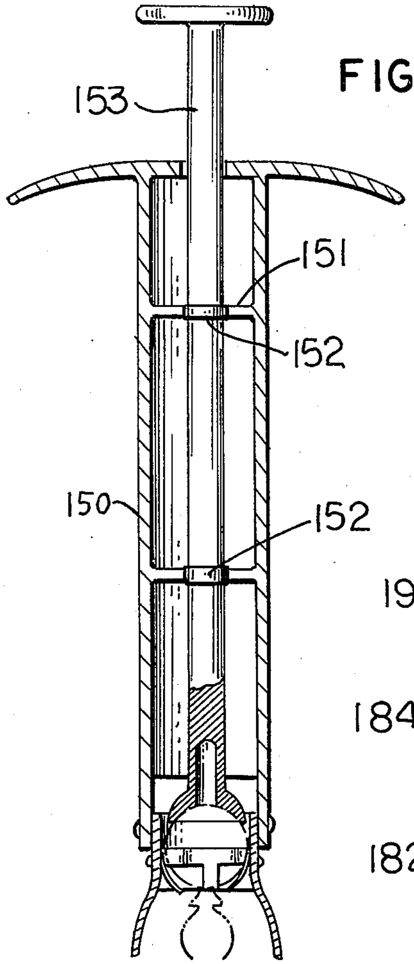
FIG. 8 is a view like FIG. 6, but showing a modification.

FIG. 8 shows a modification of the insertion device in which the tubular body part 150 has guide members 151 formed on the inside thereof, with rings 152 carried by the guide bars for guiding the insertion plunger 153.

Figure 9:
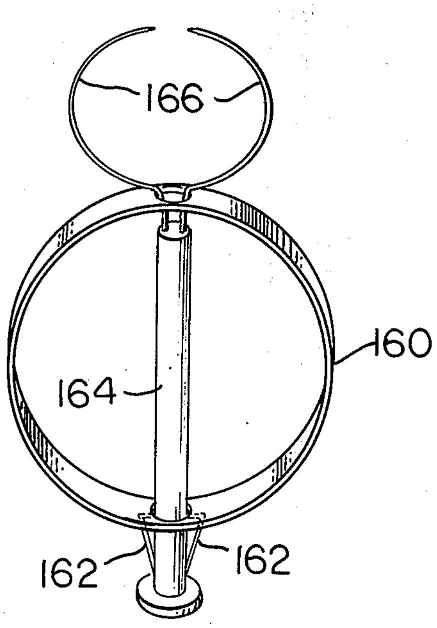
FIG. 9 is a view of a modification of the needle element utilizing a wire keeper member to hold the needle prongs together, in which the keeper element clamps on the carrier member, or handle, for the needle.
Figure 4:
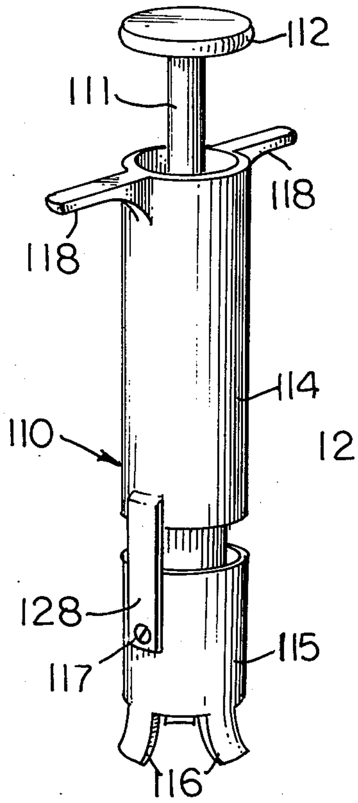
FIG. 4 is a perspective view showing an insertion device in elevation.
Figure 5:
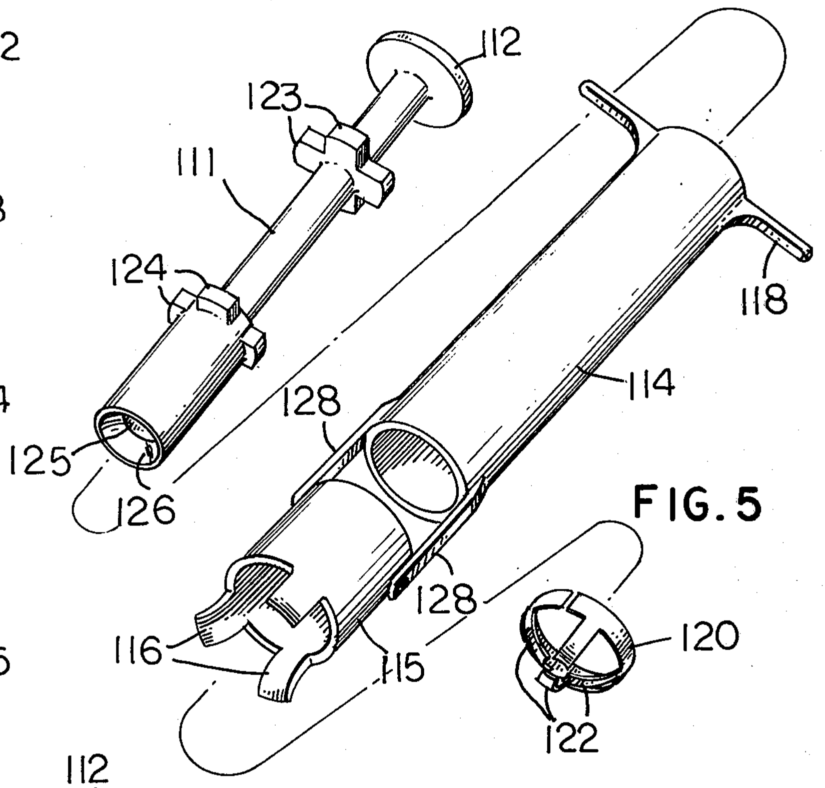
FIG. 5 is an exploded perspective view showing the various parts of the insertion device.

FIG. 9 shows a modification similar to what is disclosed in FIG. 3, except that instead of a hollow spherical bead member shown at 34 in FIG. 3, as a keeper member, a wire ring 160 is employed which has holes in opposite sides the same as the bead 34 of FIG. 3 and which is adapted for latching in advanced position by the spring elements 162 carried on the carrier member 164 to which the prongs 166 of the needle element are connected.

Figure 10:
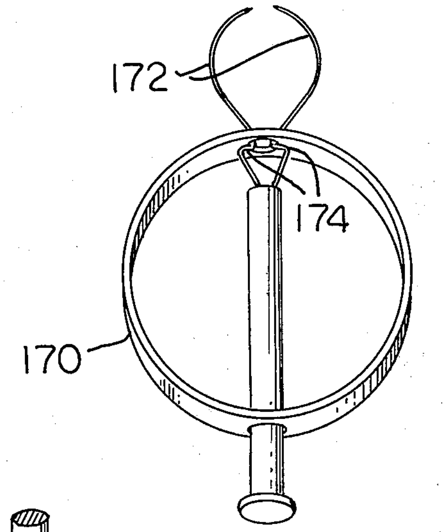
FIG. 10 is a view like FIG. 9, also showing a wire ring for a keeper member and with the keeper member arranged to latch on the needle prongs.

FIG. 10 is similar to FIG. 9 and also shows a wire ring thereon as the keeper member and is identified at 170. In this case, however, the wire ring replaces the bead member 12 of the FIGS. 1 and 2 modification and, in advanced position, latches on the prongs 172 of the needle by engaging the shoulders 174 formed directly on the needle prongs.

For removing the needles of FIGS. 1, 2 and 3, the bead member thereon is fractured, or crushed, thereby releasing the needle prongs. With the modifications of FIGS. 9 and 10, removing of the needle is accomplished by cutting the wire keeper member, thereby releasing the needle prongs.

FIGS. 11 through 14 show arrangements wherein the waist member at the lower end of the insertion device is readily detachable from the tubular barrel of the insertion device so that a waist member can be packaged with each needle in sterilized condition with the waist member being discarded after the needle therein has been inserted.

Figure 11:
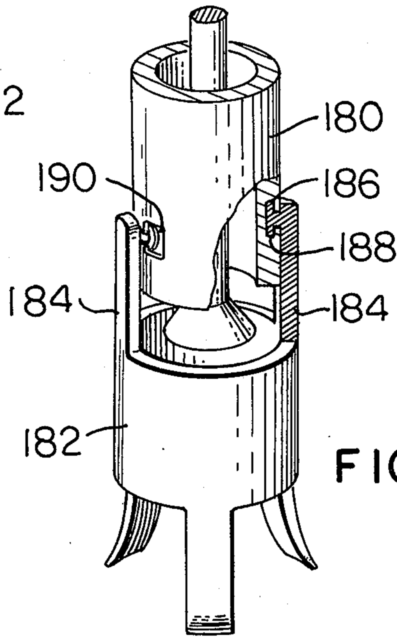
FIG. 11 is a fragmentary view showing a modified form of the insertion device.
Figure 12:
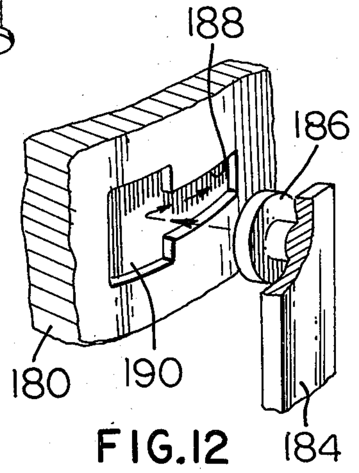
FIG. 12 is a view showing operative elements of the FIG. 11 construction.

In FIG. 11, the tubular barrel of the insertion device is indicated at 180, and the waist member containing the needle and packaged therewith in sterilized condition is indicated at 182. The waist member has prongs 184 thereon which have inwardly turned upper ends with enlarged regions 186. The inturned ends and the enlarged regions are receivable in T slots 188 formed in the tubular body 180 with at least one of the T slots having an enlarged entrance region 190 to facilitate assembling of the waist member with a tubular body of the insertion device. In all other respects the insertion device of FIGS. 11 and 12 is the same as that previously described.

Figure 13:
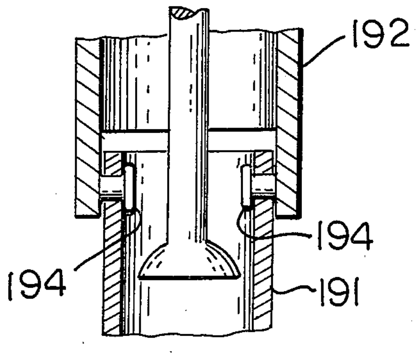
FIG. 13 shows another modification of the insertion device.

In FIG. 13, the waist member 191 is detachably receivable inside the lower end of the tubular body part 192 of the insertion device and may be retained therein as by cooperating elements of a bayonet latch formed on the waist element 191 and tubular body part 192 as indicated at 194 in FIG. 13.

Figure 14:
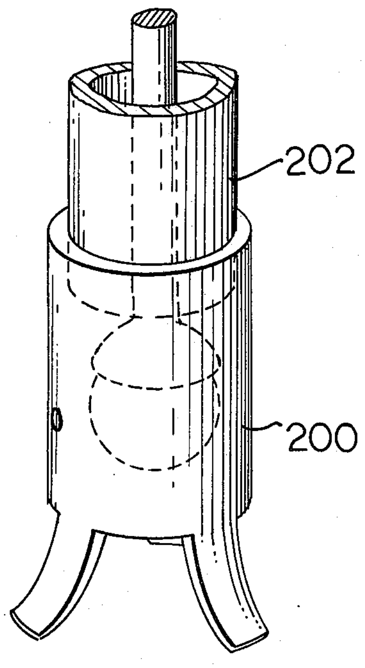
FIG. 14 is an elevational view showing still another form of the insertion device.

In FIG. 14, the waist member 200 fits over the outside of the lower end of the body part 202 and is detachably retained thereon by any suitable latch means.

From the foregoing, it will be appreciated that the practice of the method of the present invention and the use of the special needle structure and insertion device of the present invention reduces the conditions which can lead to a high incident of infection while making it simpler to place and insert the needle. The insertion of a needle according to the present invention can often be done without the use of anaesthetic, the needle and insertion device are relatively inexpensive to construct, and no special skill is required and no particular risk is involved in removing the needle.

The needle of the present invention with the opposed pointed prongs makes it simple to fix the needle in place without requiring a covering tape, or the like, thereby simplifying keeping of the area about the needle sanitary.

The needle can be inserted by the injector device of the present invention, which is stabilized by direct engagement of the legs thereof with the surface surrounding the region where needle implacement occurs. The chance of infection is greatly reduced because the needles are sterilized prior to insertion and the region where the needle is inserted can readily be cleaned since no covering tape is required.

In particular, the needle handle is conveniently located for patient manipulation to effect stimulation. Further, the implaced needle is cosmetically acceptable and manipulation of the needle by the patient for stimulation purposes is effected without any touching of that part of the needle immediately adjacent the implanted region.

Modifications may be made within the scope of the appended claims, for example, the tip of the clip needle can be blunt so that it may be held by a squeezing action on the surface of the external ear without penetrating the skin and serve the same purpose at the desired location.

What is claimed is:

1. An acupuncture needle comprising; a pair of prongs having opposed pointed tips at one end, said tips adapted to be implanted into a selected region of a human or animal body, a handle connected to the other end of said prongs, said prongs including portions diverging outwardly in a direction away from said handle and toward said pointed tips, a frangible keeper member slidable on said handle and having a region engaging said diverging portions of said prongs whereby advancing of the keeper member along said diverging portions toward said pointed tips will move said pointed tips of the prongs toward each other while maintaining them spaced from each other, and means for latching said keeper member in advanced position along said prongs, said keeper member adapted to be destroyed for removing the acupuncture needle after it has been implanted into a selected region thereby preventing further use of the needle.

2. An acupuncture needle according to claim 1 in which said handle includes means to hold said keeper member captive thereon prior to said advancing of the keeper member on said handle.

3. An acupuncture needle according to claim 1 in which said prongs are curved so as to be concave toward each other.

4. An acupuncture needle according to claim 1 in which said keeper member includes an aperture formed therein through which said portions of said prongs extend, said prongs having offset regions formed thereon at the ends of said portions nearest said pointed tips and engageable with said keeper member adjacent said aperture in advanced position of said keeper member to latch said keeper member in advanced position.

5. An acupuncture needle according to claim 1 in which said keeper member includes an aperture formed therein through which said portions of said prongs extend, said keeper member having a second aperture formed therein in which said handle is slidable, and latching spring means on said handle engageable with the side of said keeper member which faces away from said prongs in advanced position of said keeper member to latch said keeper member in advanced position.

* * * * *